US00PP27691P2

(12) United States Plant Patent
Kobayashi

(10) Patent No.: US PP27,691 P2
(45) Date of Patent: Feb. 21, 2017

(54) **NEW GUINEA *IMPATIENS* PLANT NAMED 'DUESSPSAL'**

(50) Latin Name: *Impatiens×hybrida*
Varietal Denomination: Duesspsal

(71) Applicant: Ruth Kobayashi, Carlsbad, CA (US)

(72) Inventor: Ruth Kobayashi, Carlsbad, CA (US)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 14/756,469

(22) Filed: Sep. 8, 2015

(51) Int. Cl.
*A01H 5/02* (2006.01)

(52) U.S. Cl.
USPC ..... Plt./318.3

(58) Field of Classification Search
USPC ..... Plt./318.3
See application file for complete search history.

*Primary Examiner* — Anne Grunberg
(74) *Attorney, Agent, or Firm* — C. A. Whealy

(57) ABSTRACT

A new and distinct cultivar of *Impatiens* plant named 'Duesspsal' characterized by its upright, outwardly spreading and mounding plant habit; moderately vigorous growth habit; freely branching habit; dark green-colored leaves; early and freely flowering habit; salmon orange-colored flowers; and good garden performance.

1 Drawing Sheet

Botanical designation: *Impatiens×hybrida.*
Cultivar denomination: 'DUESSPSAL'.

CROSS-REFERENCED TO CLOSELY RELATED APPLICATIONS

Title: New Guinea *Impatiens* Plant Named 'Duessplavaur'
Applicant: Ruth Kobayashi
Filed: Sep. 8, 2015; concurrently with this application having application Ser. No. 14/756,459

BACKGROUND OF THE INVENTION

The present invention relates to a new and distinct cultivar of New Guinea *Impatiens* plant, botanically known as *Impatiens×hybrida* and hereinafter referred to by the name 'Duesspsal'.

The new *Impatiens* plant is a product of a planned breeding program conducted by the Inventor in Encinitas, Calif. The objective of the breeding program is to create new uniform *Impatiens* plants with numerous attractive flowers and good garden performance.

The new *Impatiens* plant is a naturally-occurring whole plant mutation of a proprietary selection of *Impatiens× hybrida* identified as code number NN-1163-X0000, not patented. The new *Impatiens* plant was discovered and selected by the Inventor as a single flowering plant from within a population of plants of the parent selection in a controlled greenhouse environment in Encinitas, Calif. on Nov. 24, 2014.

Asexual reproduction of the new *Impatiens* plant by terminal vegetative cuttings in a controlled greenhouse environment in Encinitas, Calif. since Dec. 5, 2014 has shown that the unique features of this new *Impatiens* plant are stable and reproduced true to type in successive generations.

SUMMARY OF THE INVENTION

Plants of the new *Impatiens* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Duesspsal'. These characteristics in combination distinguish 'Duesspsal' as a new and distinct *Impatiens* plant:

1. Upright, outwardly spreading and mounding plant habit.
2. Moderately vigorous growth habit.
3. Freely branching habit.
4. Dark green-colored leaves.
5. Early and freely flowering habit.
6. Salmon orange-colored flowers.
7. Good garden performance.

Plants of the new *Impatiens* can be compared to plants of the parent selection. Plants of the new *Impatiens* differ primarily from plants of the parent selection in flower color as plants of the parent selection have light pink-colored flowers.

Plants of the new *Impatiens* can be compared to plants of *Impatiens×hybrida* 'Duessplavaur', disclosed in a U.S. Plant Patent application filed concurrently having application Ser. No. 14/756,459. Plants of the new *Impatiens* differ primarily from plants of 'Duessplavaur' in flower color as plants of 'Duessplavaur' have light lavender-colored flowers with purple-colored petal centers and margins and red purple-colored petal bases.

Plants of the new *Impatiens* can also be compared to plants of *Impatiens hawkeri* 'Kizeg', disclosed in U.S. Plant Pat. No. 11,936. In side-by-side comparisons conducted in Encinitas, Calif., plants of the new *Impatiens* differed primarily from plants of 'Kizeg' in the following characteristics:

1. Plants of the new *Impatiens* were more compact than plants of 'Kizeg'.
2. Plants of the new *Impatiens* flowered two weeks earlier than plants of 'Kizeg'.

3. Plants of the new *Impatiens* and 'Kizeg' differed in flower color as plants of 'Kizeg' have dark pink-colored flowers.

Plants of the new *Impatiens* can be compared to plants of *Impatiens×hybrida* 'SAKIMP005', disclosed in U.S. Plant Pat. No. 19,500. In side-by-side comparisons conducted in Encinitas, Calif., plants of the new *Impatiens* differed primarily from plants of 'SAKIMP005' in the following characteristics:

1. Plants of the new *Impatiens* were more compact than plants of 'SAKIMP005'.
2. Plants of the new *Impatiens* and 'SAKIMP005' differed in leaf color as plants of 'SAKIMP005' have variegated leaves.
3. Plants of the new *Impatiens* flowered two weeks earlier than plants of 'SAKIMP005'.
4. Plants of the new *Impatiens* and 'SAKIMP005' differed in flower color as plants of 'SAKIMP005' have pinkish red-colored flowers.

BRIEF DESCRIPTION OF THE PHOTOGRAPHS

The accompanying colored photographs illustrate the overall appearance of the new *Impatiens* plant showing the colors as true as it is reasonably possible to obtain in colored reproductions of this type. Colors in the photographs may differ slightly from the color values cited in the detailed botanical description which accurately describe the colors of the new *Impatiens* plant.

The photograph at the bottom of the sheet is a side perspective view of a typical flowering plant of 'Duesspsal' grown in a container.

The photograph at the top of the sheet is a close-up view of a typical flowering plant of 'Duesspsal'.

DETAILED BOTANICAL DESCRIPTION

The aforementioned photographs and following observations, measurements and values describe plants grown during the summer in 15.25-cm containers in a polyethylene-covered greenhouse in Encinitas, Calif. and under cultural practices typical of commercial New Guinea *Impatiens* production. During the production of the plants, day temperatures ranged from 24° C. to 27° C., night temperatures averaged 18° C. and light levels averaged 4,000 foot-candles. Plants were ten weeks old when the photographs and description were taken. In the following description, color references are made to The Royal Horticultural Society Colour Chart, 2007 Edition, except where general terms of ordinary dictionary significance are used.

Botanical classification: *Impatiens×hybrida* 'Duesspsal'.

Parentage: Naturally-occurring whole plant mutation of a proprietary selection of *Impatiens×hybrida* identified as code number NN-1163-X0000, not patented.

Propagation:

*Type*.—By terminal cuttings.

*Time to initiate roots, summer and winter*.—About five to seven days at day temperatures about 27° C. and night temperatures about 20° C.

*Time to produce a rooted young plant, summer and winter*.—About three weeks at day temperatures about 27° C. and night temperatures about 20° C.

*Root description*.—Fine, fibrous; white in color, actual color of the roots is dependent on substrate composition, water quality, fertilizer type and formulation, substrate temperature and physiological age of roots.

*Rooting habit*.—Freely branching; dense.

Plant description:

*Plant and growth habit*.—Upright to outwardly spreading and mounding plant habit; freely branching habit with about seven lateral branches developing per plant; moderately vigorous growth habit.

*Plant height*.—About 21.6 cm.

*Plant diameter*.—About 44 cm.

Lateral branch description:

*Length*.—About 19 cm.

*Diameter*.—About 1.1 cm.

*Internode length*.—About 3.9 cm.

*Strength*.—Strong.

*Aspect*.—Initially upright to outwardly spreading.

*Texture*.—Smooth, glabrous.

*Color*.—Close to 187A.

Leaf description:

*Arrangement*.—Opposite or in whorls; simple.

*Length*.—About 10.6 cm.

*Width*.—About 5.4 cm.

*Shape*.—Elliptical.

*Apex*.—Acuminate.

*Base*.—Attenuate.

*Margin*.—Serrulate with ciliation.

*Texture, upper and lower surfaces*.—Smooth, glabrous.

*Luster, upper surface*.—Somewhat glossy.

*Luster, lower surface*.—Matte.

*Venation pattern*.—Pinnate; arcuate.

*Color*.—Developing leaves, upper surface: Close to 146A. Developing leaves, lower surface: Close to 187B. Fully opened leaves, upper surface: Close to 139A; venation, close to 186C. Fully opened leaves, lower surface: Close to 187B; venation, close to 187C.

*Petiole length*.—About 2.5 cm.

*Petiole diameter*.—About 5 mm.

*Petiole texture, upper and lower surfaces*.—Smooth, glabrous.

*Petiole color, upper and lower surfaces*.—Close to 187C.

Flower description:

*Flower type and flowering habit*.—Single rounded and flat axillary flowers; freely flowering habit, typically about 38 flower buds and open flowers per plant at one time; flowers positioned above and beyond the foliar plane, flowers typically face mostly upright to outwardly.

*Flower longevity*.—Flowers typically last about one to two days on the plant under greenhouse conditions; petals self-cleaning, gynoecium persistent.

*Fragrance*.—None detected.

*Natural flowering season*.—Year-round under greenhouse conditions; in the garden, flowering from spring until fall in temperate regions; early flowering habit, plants typically begin flowering about eight weeks after planting.

*Flower buds*.—Length: About 1.8 cm. Diameter: About 1.6 cm. Shape: Ovoid, pointed. Color: Close to 51B.

*Flower diameter*.—About 5 cm by 5.7 cm.

*Flower depth*.—About 1.4 cm.

*Petals*.—Quantity and arrangement: Five per flower in a single whorl; one upper banner petal, two lateral petals and two lower petals. Length, banner petal: About 2.5 cm. Width, banner petal: About 3.5 cm. Length, lateral petals: About 2.6 cm. Width, lateral petals: About 2.3 cm. Length, lower petals: About 3.3 cm. Width, lower petals: About 3.1 cm. Shape: Cordate. Apex: Cordate; emarginate. Base: Attenuate. Margin: Entire. Texture, upper and lower surfaces: Smooth, glabrous; velvety. Color: When opening, upper surface: Close to 43B. When opening, lower surface: Close to 50C. Fully opened, upper surface: Close to 43B to 43C; towards the base, close to 44B; color does not change with development. Fully opened, lower surface: Close to 51C; color does not change with development.

*Sepals*.—Quantity and arrangement: Three in a single whorl; one modified into an elongated spur. Length: About 2 cm. Width: About 5 mm. Shape: Narrowly deltoid. Apex: Apiculate. Base: Attenuate. Margin: Entire. Texture, upper and lower surfaces: Smooth, glabrous. Color, upper and lower surfaces: Close to 145D. Spur length: About 5.5 cm. Spur diameter: At the flower, about 3 mm; towards the apex, about 1 mm. Spur texture: Smooth, glabrous. Spur color: Close to 145D.

*Peduncles*.—Length: About 4.5 cm. Diameter: About 2 mm to 3 mm. Angle: About 35° to 45° from stem axis. Strength: Strong; flexible. Texture: Smooth, glabrous. Color: Close to 146C.

*Reproductive organs*.—Stamens: Quantity: Five fused at anthers; filaments free. Filament length: Less than 1 mm. Filament color: Close to 1D. Anther size: About 4 mm by 6 mm. Anther shape: Oblong. Anther color: Close to 63A. Pollen amount: Moderate. Pollen color: Close to 158B. Pistils: Quantity per flower: One. Pistil length: About 5 mm. Stigma shape: Rounded. Stigma color: Close to 155C. Style color: Close to 146A. Ovary color: Close to 146A.

*Seeds and fruits*.—Seed and fruit production has not been observed on plants of the new *Impatiens*.

Disease & pest resistance: Plants of the new *Impatiens* have not been observed to be resistant to pathogens and pests common to *Impatiens* plants.

Garden performance: Plants of the new *Impatiens* have been observed to have good garden performance and tolerate temperatures ranging from about 5° C. to about 40° C.

It is claimed:

1. A new and distinct *Impatiens* plant named 'Duesspsal' as illustrated and described.

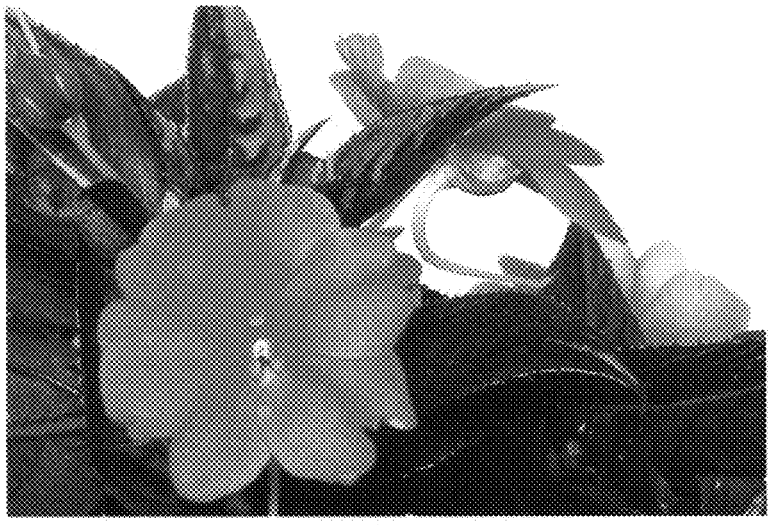
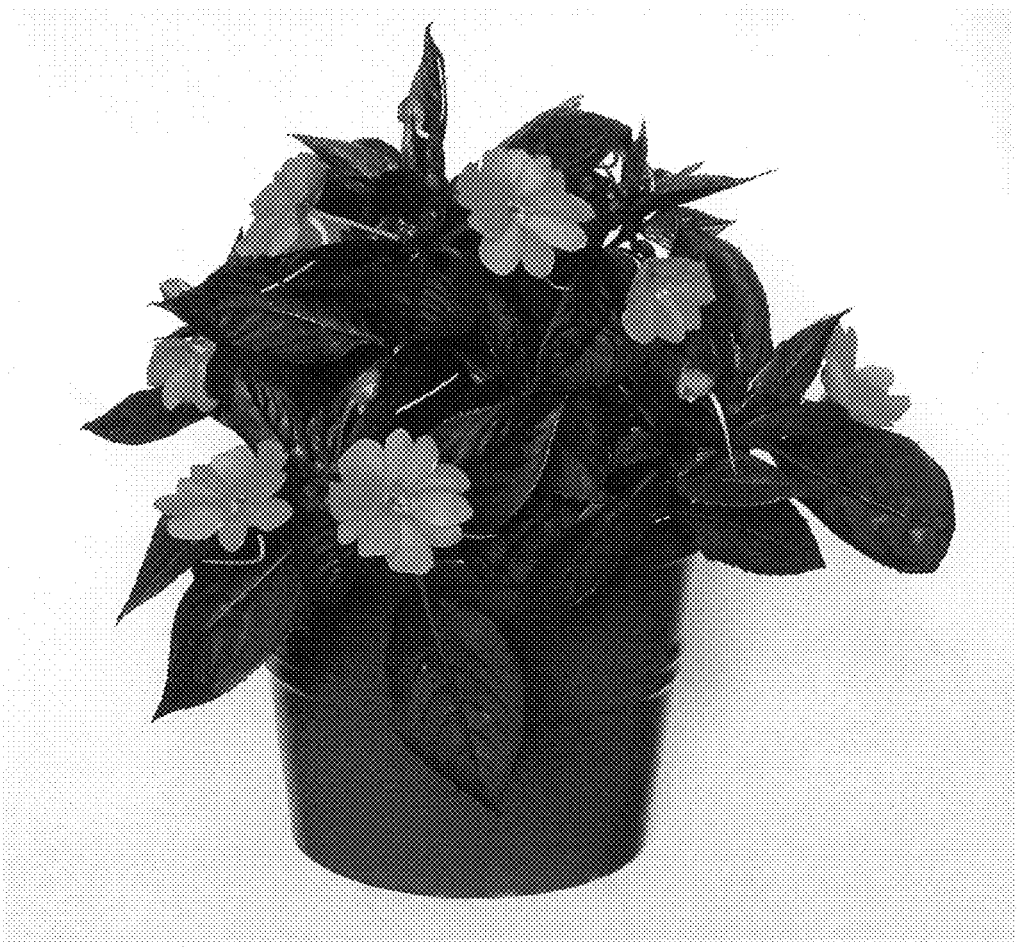

* * * * *